United States Patent

Hubele et al.

[11] Patent Number: 4,546,109
[45] Date of Patent: Oct. 8, 1985

[54] ORGANOTIN COMPOUNDS AND PESTICIDAL COMPOSITIONS

[75] Inventors: Adolf Hubele, Magden; Peter Riebli, Buckten, both of Switzerland

[73] Assignee: Ciba-Geigy Corporation, Ardsley, N.Y.

[21] Appl. No.: 504,021

[22] Filed: Jun. 13, 1983

[30] Foreign Application Priority Data

Jun. 22, 1982 [CH] Switzerland .......................... 3820/82

[51] Int. Cl.$^4$ ...................... C07F 7/22; A01N 55/04; A61K 31/32
[52] U.S. Cl. ........................................ 514/493; 556/94
[58] Field of Search ....................... 260/429.7; 424/288

[56] References Cited

U.S. PATENT DOCUMENTS

| | | | |
|---|---|---|---|
| 2,507,055 | 5/1950 | Smith et al. | 260/429.7 X |
| 3,435,037 | 3/1969 | Langer et al. | 260/429.7 X |
| 3,446,827 | 5/1969 | Schwartz | 260/429.7 |
| 3,499,086 | 3/1970 | Brueckner et al. | 424/286 |
| 4,472,429 | 9/1984 | Drabek | 260/429.7 X |

OTHER PUBLICATIONS

Poller, The Chemistry of Organotin Compounds, Academic Press, N.Y., pp. 173–178, (1970).
Chemical Abstracts, 101, 111204t, (1984).

Primary Examiner—Helen M. S. Sneed
Attorney, Agent, or Firm—Edward McC. Roberts

[57] ABSTRACT

There are described novel organotin compounds of the formula I

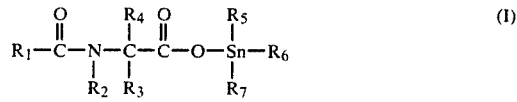

wherein
- $R_1$ is unsubstituted or substituted lower alkyl, lower alkenyl, cycloalkyl, furyl or tetrahydrofuryl;
- $R_2$ is unsubstituted or substituted aryl;
- $R_3$ and $R_4$ independently of one another are each hydrogen, or unsubstituted or substituted lower alkyl; and
- $R_5$, $R_6$ and $R_7$ independently of one another are each unsubstituted or substituted lower alkyl, cycloalkyl or aryl.

There are also disclosed methods of producing these products, and also pesticidal compositions containing one of the said compounds as active ingredient. Also described is a method for controlling plant pests, which method is based on the application of the stated active substances or of compositions prepared therefrom.

15 Claims, No Drawings

ORGANOTIN COMPOUNDS AND PESTICIDAL COMPOSITIONS

The present invention relates to novel organotin compounds of the formula I given below. It relates also to the production thereof and also to pesticidal compositions containing at least one of these substances as active ingredient. This invention relates also to the production of the said compositions, and to the use thereof and/or of the novel active substances for controlling pests in the field of agriculture, for example for the control of fungi which damage plants and stored foodstuffs, and of bacteria and/or insects.

The novel organotin compounds according to the invention have the formula I

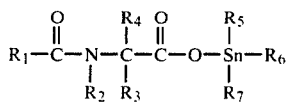

wherein $R_1$ is unsubstituted or substituted lower alkyl, lower alkenyl, cycloalkyl, furyl or tetrahydrofuryl;

$R_2$ is unsubstituted or substituted aryl;

$R_3$ and $R_4$ independently of one another are each hydrogen, or unsubstituted or substituted lower alkyl; and $R_5$, $R_6$ and $R_7$ independently of one another are each unsubstituted or substituted lower alkyl, cycloalkyl or aryl.

The term "lower" in front of an aliphatic substituent is to denote here and in the following a straight-chain or branched-chain radical having a maximum of 8 carbon atoms. Lower alkyl is thus preferably $C_1$-$C_8$-alkyl, such as methyl, ethyl, propyl, butyl, pentyl, hexyl, heptyl or octyl, as well as isomers thereof, such as isopropyl, isobutyl, tert-butyl, isopentyl, and so forth. Lower alkenyl is in particular $C_2$-$C_8$-alkenyl, for example vinyl, propenyl-(1), allyl, butenyl-(1), butenyl-(2), butenyl-(3), and so on; and also straight or branched chains having several double bonds. Cycloalkyl here and in the following is especially $C_3$-$C_7$-cycloalkyl, for example cyclopropyl, cyclobutyl, cyclopentyl, cyclohexyl, cycloheptyl, and so forth: preferably however cyclopropyl, cyclopentyl and cyclohexyl. Furyl is preferably 2-furyl or tetrahydrofuryl, particularly 2-tetrahydrofuryl. Aryl is preferably phenyl or naphthyl, naphthyl embracing both α-naphthyl and β-naphthyl.

By a substituted lower alkyl group is meant in this case a straight-chain or branched-chain $C_1$-$C_6$-alkyl group, especially propyl or ethyl, and particularly preferably methyl; and as substituents of these lower alkyl groups, the following radicals are for example preferred: hydroxyl; $C_1$-$C_6$-alkoxy, preferably $C_1$-$C_4$-alkoxy, particularly ethoxy and methoxy; $C_3$-$C_4$-alkenyloxy, especially allyloxy; $C_3$-$C_6$-alkynyloxy, in particular propargyloxy; $C_1$-$C_3$-alkoxy-($C_1$-$C_3$-alkoxy), such as $CH_3OCH_2CH_2O$ or $CH_3OCH_2O$; $C_1$-$C_6$-alkylthio, preferably $C_1$-$C_4$-alkylthio, especially ethylthio and methylthio; $C_1$-$C_4$-alkylsulfonyloxy, in particular $OSO_2C_2H_5$ and $OSO_2CH_3$, preferably $OSO_2CH_3$; $C_1$-$C_4$-alkylaminosulfonyloxy, such as $OSO_2NH(C_1$-$C_3$-alkyl), for example $OSO_2NHC_3H_7$, $OSO_2NHC_2H_5$ or in particular $OSO_2NHCH_3$; $C_1$-$C_4$-alkylsulfonyl, especially —$SO_2C_2H_5$ and —$SO_2CH_3$; $C_1$-$C_4$-alkylsulfoxy, particularly —$SOC_2H_5$ and $SOCH_3$; halogen, such as fluorine, chlorine, bromine or iodine, preferably chlorine; phenyl; phenoxy; benzyloxy; azolyl, such as triazolyl or imidazolyl, preferably 1H-1,2,4-triazolyl and 1H-imidazolyl. Particularly preferred substituents for the lower alkenyl and cycloalkyl groups are: halogen atoms, such as fluorine, chlorine, bromine or iodine, especially chlorine or bromine. Preferred substituents for furyl and tetrahydrofuryl are in particular halogen (especially bromine), $C_1$-$C_4$-alkoxy (particularly ethoxy and methoxy), as well as the nitro groups. Particularly preferred substituents for aryl radicals are: halogen atoms, such as fluorine, chlorine, bromine or iodine, especially chlorine or bromine, as well as $C_1$-$C_3$-alkoxy, particularly methoxy; $C_1$-$C_3$-alkyl, especially methyl and $C_1$-$C_3$-haloalkyl, in particular trifluoromethyl, whereby identical or different substituents can occur in the same aryl moiety. Particularly preferred radicals for the —$Sn(R_5)(R_6)(R_7)$ group are $C_1$-$C_6$-alkyl, especially methyl, butyl and cyclohexyl, as well as in particular the phenyl group, those groupings wherein $R_5$, $R_6$ and $R_7$ are identical being more especially preferred. Preferred radicals $R_3$ and $R_4$ are hydrogen, $C_1$-$C_4$-alkyl, or $C_1$-$C_3$-alkyl which is unsubstituted or substituted by halogen (particularly chlorine or bromine), hydroxyl, mercapto, $C_1$-$C_4$-alkoxy, $C_1$-$C_4$-alkylthio, $C_1$-$C_3$-alkoxy-($C_1$-$C_3$-alkoxy), $C_1$-$C_3$-alkoxy-($C_1$-$C_3$-alkylthio), $C_1$-$C_4$-alkylcarbonyloxy, $C_1$-$C_4$-carbamoyloxy or $C_1$-$C_4$-alkoxycarbonyloxy. Especially preferred are combinations in which one of the radicals $R_3$ and $R_4$ is hydrogen.

By alkyl itself or by alkyl moiety of another substituent are in general meant, depending on the given number of carbon atoms, for example the following groups: methyl, ethyl, propyl, butyl, pentyl, hexyl, heptyl, octyl, and so forth, and isomers thereof, such as isopropyl, isobutyl, tert-butyl, isopentyl, and so on. Haloalkyl is a mono- to perhalogenated alkyl substituent, for example: $CHCl_2$, $CHF_2$, $CH_2Cl$, $CCl_3$, $CH_2F$, $CH_2CH_2Cl$, $CHBr_2$, and so forth, especially $CF_3$. Halogen denotes here and in the following: fluorine, chlorine, bromine or iodine, preferably fluorine, chlorine or bromine. Alkenyl is for example: propenyl-(1), allyl, butenyl-(1), butenyl-(2) or butenyl-(3).

The compounds of the formula I are at room temperature stable oils, resins or mainly solids, which in each case are distinguished by very valuable microbicidal and growth-regulating properties. They can be used in agriculture and in related fields, in a preventive and curative manner, for controlling pests, such as insects, bacteria and in particular phytopathogenic fungi, the 2,6-disubstituted aniline derivatives within the scope of the formula I being preferred. The active substances of the formula I are characterised by having very good compatibility with cultivated plants, and a high level of activity against specific Oomycetes fungus strains resistant to chemicals.

Preferred by virtue of their marked activity against plant pests are the following subgroups of compounds of the formula I in order of preference, the group Id being most preferred:

group Ia, consisting of compounds of the formula I wherein $R_1$ is methyl substituted by chlorine, methoxy, ethoxy, $CH_2=CHCH_2O—$, $HC≡CCH_2O—$, $CH_3OCH_2O—$, methylsulfonyl, methylsulfonyloxy, methylaminosulfonyloxy, methylthio or 1H-1,2,4-triazolyl, or $R_1$ is $C_2$-$C_4$-alkenyl, $C_2$-$C_4$-alkenyl substituted by chlorine, or it is $C_3$-$C_6$-cycloalkyl, unsubstituted 2-tetrahydrofuryl, or 2-furyl which is unsubstituted or substituted by bromine, $R_2$ is phenyl which is substituted in both ortho-positions, and optionally additionally in the metha-position, by chlorine, methyl, methoxy, —$CF_3$ and/or nitro, or $R_2$ is α-naphthyl substituted in the ortho-position by chlorine, methyl, methoxy, —$CF_3$ or nitro, $R_3$ is hydrogen, $C_1$-$C_2$-alkyl, hydroxyethyl, methoxyethyl, methoxymethyl or chloroethyl, $R_4$ is hydrogen, and $R_5$, $R_6$ and $R_7$ independently of one another are each methyl, n-butyl, cyclohexyl or phenyl;

group Ib, consisting of compounds of the formula I wherein $R_1$ is methyl substituted by chlorine, methoxy, ethoxy, $CH_2$=$CHCH_2O$—, $HC$≡$CCH_2O$—, methoxymethoxy or 1H-1,2,4-triazolyl, or $R_1$ is cyclopropyl, 2-furyl or 2-tetrahydrofuryl, $R_2$ is phenyl diortho-substituted by chlorine, methyl, methoxy, $CF_3$ and/or nitro, $R_3$ is hydrogen, $C_1$-$C_2$-alkyl, hydroxyethyl, methoxyethyl, methoxymethyl or chloroethyl, $R_4$ is hydrogen, and $R_5$, $R_6$ and $R_7$ independently of one another are each methyl, n-butyl, cyclohexyl or phenyl;

group Ic, consisting of compounds of the formula I wherein $R_1$ is methoxymethyl, $R_2$ is phenyl diortho-substituted by chlorine, methyl, methoxy, $CF_3$ and/or nitro, $R_3$ is methyl or hydroxymethyl, $R_4$ is hydrogen, and $R_5$, $R_6$ and $R_7$ independently of one another are each $C_1$-$C_4$-alkyl, $C_3$-$C_6$-cycloalkyl or phenyl;

group Id, consisting of compounds of the formula I wherein $R_1$ is methoxymethyl, $R_2$ is 2,6-dimethylphenyl, $R_3$ is methyl or hydroxymethyl, $R_4$ is hydrogen, and $R_5$, $R_6$ and $R_7$ are each $C_1$-$C_4$-alkyl or phenyl.

The following individual substances are particularly preferred on account of their pronounced activity against plant pests:

N-(1'-triphenyltinoxycarbonylethyl)-N-methoxyacetyl-2,6-dimethylaniline,

N-[1'-triphenyltinoxycarbonyl-(prop-3-ol-1-yl)]-N-methoxyacetyl-2,6-dimethylaniline, N-(1'-trimethyltinoxycarbonylethyl)-N-methoxyacetyl-2,6-dimethylaniline, N-[1'-tri-n-butyltinoxycarbonyl-(prop-3-ol-1-yl)]-N-methoxyacetyl-2,6-dimethylaniline, N-(1'-tri-n-butyltinoxycarbonylethyl)-N-methoxyacetyl-2,6-dimethylaniline, and N-[1'-trimethyltinoxycarbonyl-(prop-3-ol-1-yl)]-N-methoxyacetyl-2,6-dimethylaniline.

The compounds of the formula I are produced according to the invention:

(A) by reaction of a compound of the formula II

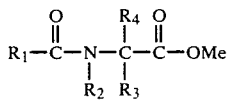

(II)

wherein $R_1$, $R_2$, $R_3$ and $R_4$ are as defined under the formula I, and Me is hydrogen, or a metal atom, preferably an alkali metal atom or alkaline-earth metal atom, such as Li, Na, K, Ca, Mg, and so forth, with a triorganyltin halide of the formula III

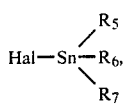

(III)

wherein $R_5$, $R_6$ and $R_7$ are as defined under the formula I, and Hal is halogen, especially chlorine or bromine, preferably chlorine, and whereby in the cases in which Me is hydrogen, the reaction is performed preferably in the presence of an acid-binding agent; or (B) by an N-acylation reaction of a compound of the formula IV

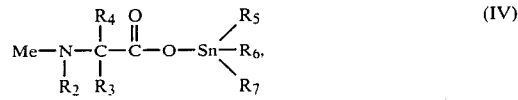

(IV)

wherein the substituents $R_2$, $R_3$, $R_4$, $R_5$, $R_6$ and $R_7$ are as defined under the formula I, and Me is hydrogen, or preferably a metal atom, especially an alkali metal atom or alkaline-earth metal atom, such as Li, Na, K, Ca, Mg, and so forth, optionally in the presence of an acid-binding agent, with a reactive acid derivative of the formula V

(V)

wherein $R_1$ is as defined under the formula I, and G is the group $R_1$—COO—, a free or esterified hydroxyl group or, preferably, a halogen atom, particularly chlorine or bromine; or (C) by reaction of a compound of the formula VI

(VI)

wherein $R_1$ and $R_2$ are as defined under the formula I, and M is hydrogen or an alkali metal atom, preferably potassium or sodium, with a compound of the formula VII

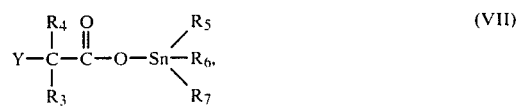

(VII)

wherein $R_3$, $R_4$, $R_5$, $R_6$ and $R_7$ are as defined under the formula I, and Y is a customary nucleofug removable group, the nucleofug removable groups used being substituents such as halogen, especially chlorine, bromine or iodine, or reactive esterified groups, such as arylsulfonyloxy or alkylsulfonyloxy or acyloxy groupings, for example benzenesulfonyloxy, p-tosyloxy or trifluoroacetyloxy, or preferably lower alkylsulfonyloxy, such as mesyloxy; and a compound of the formula I obtainable by a process according to the invention can be converted into another compound of the formula I; for example a nitrated compound converted by hydrogenation into an amino compound, a nonhalogenated compound into a halogenated compound, the last-mentioned into another halogenated compound; or a product produced for example according to variant A and corresponding to the formula Ia

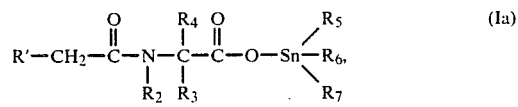

(Ia)

wherein R' is halogen or a free or esterified hydroxyl or mercapto group, and the other substituents are as defined under the formula I, can be converted with any one of the following compounds of the formulae VIIIa to VIIId

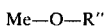  Me—O—R''  (VIIIa)

or

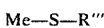  Me—S—R'''  (VIIIb)

or

  Me—azolyl  (VIIIc)

or

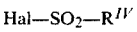  Hal—SO$_2$—R$^{IV}$  (CIIId), wherein Me is preferably an alkali metal atom, in particular potassium or sodium, R$_2$ is especially C$_1$–C$_6$-alkyl, C$_3$–C$_4$-alkenyl, C$_3$–C$_6$-alkynyl, phenyl, benzyl or C$_1$–C$_3$-alkoxy-(C$_1$–C$_3$-alkyl), R''' is particularly C$_1$–C$_6$-alkyl, 'azolyl' is preferably 1H-imidazolyl or 1H-1,2,4-triazolyl, R$^{IV}$ is especially an amino group substituted by C$_1$–C$_4$-alkyl, and Hal is halogen, preferably chlorine or bromine, into a corresponding product of the formula I, whereby products having a sulfur bridge can be also subsequently further oxidised.

Other conversions of compounds of the formula I into further compounds of the formula I are for example the reactions of compounds of the formula Ib

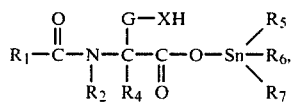

wherein the substituents R$_1$, R$_2$, R$_4$, R$_5$, R$_6$ and R$_7$ are as defined under the formula I, G is a C$_1$–C$_4$-alkylene bridge, and X is oxygen or sulfur, with preferably one of the following compounds of the formula IXa or IXb

  Hal—R$^V$  (IXa)

or

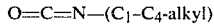  O=C=N—(C$_1$–C$_4$-alkyl)  (IXb), wherein Hal is a halogen atom, preferably chlorine or bromine, and R$^V$ is preferably C$_1$–C$_4$-alkyl, C$_2$–C$_6$-alkoxyalkyl, C$_1$–C$_4$-alkylcarbonyl, C$_1$–C$_4$-carbamoyl or C$_1$–C$_4$-alkoxycarbonyl. Furthermore, other conversions can be carried out: such conversion reactions can thus be performed also on the intermediate products II, IV or VII, before these are further reacted to the final products.

The production variant A is generally performed at temperatures of 0° to 80° C., preferably 10° to 30° C.; variant B at 0° to 180° C., preferably 20° to 120° C. or at the reflux temperature of the reaction medium, and the variant C at 20° to 130° C., preferably 80° to 120° C. or at the reflux temperature of the reaction medium.

In the case of variants A, B and C, the use of an acid-binding agent is advantageous. Suitable as such are organic and inorganic bases, for example tertiary amines, such as trialkylamines (trimethylamine, triethylamine, tripropylamine, and so forth), pyridine and pyridine bases (4-dimethylaminopyridine, 4-pyrrolidylaminopyridine, and so on), oxides and hydroxides, carbonates and hydrogen carbonates of alkali metals and alkaline-earth metals, and also alkali acetates.

Formed hydrogen halide can in some cases be expelled from the reaction medium also by inert gas, for example nitrogen, being passed through.

The reactions are advantageously performed in the presence of solvents or diluents inert to the reactants. Suitable solvents or diluents are for example: aliphatic and aromatic hydrocarbons, such as benzene, toluene, xylenes or petroleum ether; halogenated hydrocarbons, such as chlorobenzene, methylene chloride, ethylene chloride, chloroform, carbon tetrachloride or tetrachloroethylene; ethers and ethereal compounds, such as dialkyl ethers (diethyl ether, diisopropyl ether, tert-butylmethyl ether, and so forth), anisole, dioxane and tetrahydrofuran; nitriles, such as acetonitrile or propionitrile; in some cases N,N-alkylated amides, such as dimethylformamide; dimethylsulfoxide; ketones, such as acetone, diethyl ketone or methyl ethyl ketone; and mixtures of such solvents with one another. The acylating agent itself can in some cases serve as solvent. It is advantageous in variant A when additionally water is present.

In the case of the acylation reactions, the presence of a reaction catalyst, such as dimethyl formamide, can be of advantage.

The starting substances of the formulae III, V, VI, VIIIa to VIIId and also IXa and IXb are known and for the most part commercially available. The compounds of the formula VII are obtainable, by a procedure analogous to that of production variant A, by reaction from the basic acids with triorganyltin halides of the formula III. The compounds of the formula II are in part known, and can be produced, by methods known per se, from the basic anilides or anilines.

All parts of the described production process form subject matter of this invention.

In the cases where the substituents R$_3$ and R$_4$ are not identical, for example R$_3$=CH$_3$ and R$_4$=H, the compounds of the formula I have, on the linking carbon atom of R$_3$ and R$_4$, an asymmetric centre, and in production are usually obtained as racemates, which can either be subsequently separated, in the customary manner, into the optical antipodes, or can be synthesised, by the use of optically pure starting materials, as optically pure antipodes. An optically pure anilide of the formula II can thus be produced for example by reaction of an optically pure α-halocarboxylic acid Hal—C(R$_3$)(R$_4$)—COOH and the corresponding acylanilide, and can then be converted, by reaction according to variant A, into the optically pure isomer of the formula I. Further asymmetric centres can occur depending on substitution. Independently of the stated optical isomerism, there is in some cases observed also an atropisomerism around the (aryl—N<) axis.

The optical antipodes I exhibit differing biocidal levels of activity. The use of racemates generally suffices for practical application, although the use of pure antipodes can lead to a lowering of the active dose.

It has been found that the organotin compounds of the formula I according to the invention surprisingly exhibit, against important phytopathogenic pests, an activity which is favourable for practical use in the agricultural field, in horticulture and in related fields, and that the said compounds are therefore suitable for the protection of growing and stored cultivated plants. The spectrum of activity extends from harmful microorganisms, such as fungi and bacteria, to insects. The compounds have very advantageous curative, systemic and, in particular, preventive properties, and can be applied for the protection of numerous cultivated plants. The microorganisms occurring on plants or on parts of plants (fruit foliage, stalks, tubers or roots) of various cultivated crops can be inhibited or destroyed with the active substances of the formula I, and also parts of plants subsequently growing remain preserved from such pests, particularly phytopathogenic microorganisms. The microbicidal activity is effective also against microorganisms which can present serious problems in the storage of vegetable and animal material.

Active substances of the formula I are active against a whole series of phytopathogenic pests; they are for example active against the fungi belonging to the following classes: Ascomycetes (for example Eryphe and Venturia); Fungi imperfecti (for example Botrytis, Helminthosporium, Fusarium and Cercospora); Basidiomycetes (for example Hemileia, Rhizoctonia and Puccinia); in particular however against Oomycetes belonging to the Phycomycetes class, such as Peronosperales (Phytophthora, Pythium and Plasmopara); and surprisingly also fungus strains resistant to acylanine can be successfully controlled. Furthermore, compounds of the formula I are effective against serious forms of mould fungus in the protection of provisions (for example Penicillium, Aspergillus, Rhizopus and Nigrospora), as well as against bacteria, such as butyric acid bacteria and Xanthomonas species, and yeasts such as Candida. One class of active substances exhibits also a marked insecticidal action. The active substances can also be used as dressing agents for the treatment of seed and stored plant material (fruit, tubers and grain), and plant cuttings to protect them from fungus infections, and also against phytopathogenic fungi and bacteria occurring in the soil.

The invention hence relates also to pesticidal compositions, and also to the use of the compounds of the formula I for controlling phytopathogenic pests, such as insects or bacteria, especially phytopathogenic fungi, and for the preventive and curative treatment of plant infestation and infection.

In addition, the present invention embraces also the production of pesticidal compositions, which comprises the intimate mixing of the active substance with one or more substances or groups of substances described herein. Also included in the scope of the invention is a process for the treatment of plants, which process is characterised by the use of the compounds of the formula I or of the novel compositions.

Within the scope of this invention, target crops with respect to the range of indications disclosed herein include for example the following species of cultivated plants: cereals: wheat, barley, rye, oats, rice, sorghum and related cereals; beet: sugar beet and fodder beet; pomaceous fruit, stone fruit and soft fruit: apples, pears, plums, peaches, almonds, cherries, strawberries, raspberries and blackberries; legumes: beans, lentils, peas and soya-bean; oil plants: rape, mustard, poppy, olives, sunflowers, coco, castor-oil plants, cocoa and groundnuts; Cucurbitacea: pumpkins, cucumbers and melons; fibre plants: cotton, flax, hemp and jute; citrus fruits: oranges, lemons, grapefruit and mandarins; varieties of vegetables: spinach, lettuce, asparagus, varieties of cabbage, carrots, onions, tomatoes, potatoes and paprika; laurel plants: avocada, cinnamon and camphor); or plants such as maize, tobacco, nuts, coffee, sugar cane, tea, grapevines, hops, bananas and natural rubber plants; and also ornamental plants (composites).

Active substances of the formula I are customarily used in the form of compositions, and can be applied, simultaneously or successively, with further active substances to the area or plants to be treated. These further active substances can be fertilisers, trace-element agents or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

Suitable carriers and additives can be solid or liquid and they correspond to the substances customarily employed in formulation practice, for example: natural or regenerated mineral substances, solvents, dispersing agents, wetting agents, adhesives, thickeners, binders or fertilisers, and also phospholipides of animal or vegetable origin.

A preferred method of applying an active substance of the formula I, or an agrochemical composition containing at least one of these active substances, is application to the foliage (leaf application). The number of applications and the amounts applied are governed by the extent of infestation with respect to the pathogen (fungus genus) concerned. The active substances of the formula I can however be fed into the plant through the soil and then by way of the root system (systemic action), this being achieved by the locus of the plant being soaked with a liquid preparation, or by the substances being introduced in solid form into the soil, for example in the form of a granulate (soil application). The compounds of the formula I can also be applied to the seed grains (coating), the grains being for this purpose either soaked with a liquid preparation of the active substance or coated with a solid preparation. Further forms of application are possible in special cases, for example the specific treatment of the stalks or buds of the plants.

The compounds of the formula I are used either in an unmodified form of preferably together with auxiliaries customarily employed in formulation practice, and are thus processed in a known manner for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions. Favourable applied amounts are in general between 50 g and 5 kg of active substance (AS) per hectare, preferably between 100 g and 2 kg of AS per hectare, and in particular between 200 g and 600 g of AS per hectare.

The formulations, that is to say, the compositions or preparations containing the active substance of the formula I and optionally a solid or liquid additive, are produced in a known manner, for example by the intimate mixing and/or grinding of the active substance with extenders, such as with solvents, solid carriers and optionally surface-active compounds (tensides).

Suitable solvents are: aromatic hydrocarbons, preferable the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to add highly dispersed silicic acid or highly dispersed absorbent polymers. Suitable granulated adsorptive carriers are porous types, for example pumice, ground brick, sepiolite or bentonite; and suitable non-sorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkyarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"Mc Cutcheon's Detergents and Emulsifiers Annual", MC Publishing Corp., Ringwood, N.J., 1980;
Sisely and Wood, "Encyclopedia of Surface Active Agents", Chemical Publishing Co., Inc. New York, 1980.

The agrochemical preparations contain as a rule 0.1 to 99%, particularly 0.1 to 95%, of active substance of the formula I, 99.9 to 1%, especially 99.8 to 5%, of a solid or liquid additive, and 0 to 25%, in particular 0.1 to 25%, of a tenside.

Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active ingredients for obtaining special effects.

Agrochemical compositions of the types described herein likewise form subject matter of the present invention.

The following Examples serve to further illustrate the invention without limiting the scope thereof. Percentage values and 'parts' relate to weight. In addition, the following symbols are used: h=hour; d=day; min=minute; RT=room temperature; N=normality; abs.=anhydrous; DMSO=dimethyl sulfoxide; DMF=dimethyl formamide. Pressure values are in millibars (mb) or bars (b).

PRODUCTION EXAMPLES

EXAMPLE α:

Production of

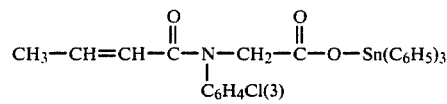

N-Triphenyltinoxycarbonylmethyl-N-crotyl-3-chloroaniline 2.4 parts of a 55% sodium hydride dispersion were added, with the passing through of nitrogen and with stirring, to a solution of 9.8 parts of crotonic acid(3-chloroanilide) in 200 ml of dioxane, and the mixture was heated at +80° C. for 2 h. It was cooled to RT and, with stirring, 25.8 parts of triphenyltin-(2-bromoacetate) were added portionwise within 1 h; the reaction mixture was subsequently heated to +60° C., diluted with 800 ml of ice-water, and extracted three times with 150 ml of methylene chloride each time. The combined extracts were washed twice with 50 ml of water each time, dried over sodium sulfate and filtered, and the solvent was evaporated off. The oily residue was shaken up in petroleum ether and crystallised. The beige crystals were filtered off and dried; m.p. 85°–91° C.

EXAMPLE β

Production of

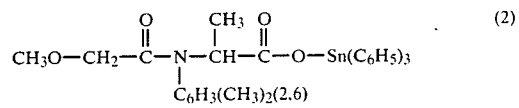 (2)

N-(1'-Triphenyltinoxycarbonylethyl)-N-methoxyacetyl-2,6-dimethylaniline 15.8 parts of triphenyltin chloride in 150 ml of methylene chloride were added dropwise at RT, with stirring, to a solution of 13 parts of the sodium salt of N-(1'-hydroxycarbonylethyl)-N-methoxyacetyl-2,6-dimethylaniline in 150 ml of water, and stirring was continued for 7 h. The organic phase was subsequently separated, washed three times with 50 ml of water each time, dried with a molecular sieve and filtered, and the solvent was then removed in vacuo. The crystalline residue was recrystallised with active charcoal from 200 ml of cyclohexane. The colourless crystals had a melting point of 129°–130° C.

EXAMPLE γ

Production of

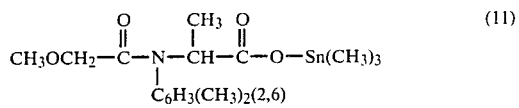 (11)

N-(1'-Trimethyltinoxycarbonylethyl)-N-methoxyacetal-2,6-dimethylaniline 18 parts of methoxyacetic acid chloride were added dropwise to 15 parts of N-(1'-trimethyltinoxycarbonylethyl)-2,6-dimethylaniline and 18 parts of triethylamine in 200 ml of toluene. After subsidence of the slightly exothermic reaction, stirring was maintained for 3 h at RT; the triethylamine hydrochloride was separated by filtration, and the reaction solution was washed twice with 50 ml of water each time; it was subsequently dried over sodium sulfate and filtered, and the solvent was evaporated off. The oily residue was shaken with ether and crystallised. The beige crystals were recrystallised from chloroform/petroleum ether (30°–50° C.) 1:1, and the resulting product melted at 136°–137° C.

The compounds of the formula I listed in the following Table 1 can be produced in an analogous manner or by any one of the described production variants.

TABLE 1

Compounds of the formula

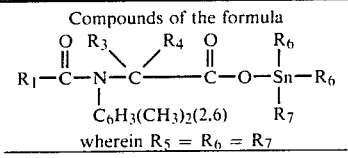

wherein $R_5 = R_6 = R_7$

| Comp. | $R_1$ | $R_3$ | $R_4$ | $R_{5,6,7}$ | Physical constants |
|---|---|---|---|---|---|
| 1 | $CH_3$ | $CH_3$ | $CH_3$ | $C_6H_5$ | |
| 2 | $CH_2OCH_3$ | $CH_3$ | H | $C_6H_5$ | m.p. 129–130° C. |
| 3 | $CH_2OCH_3$ | $C_2H_5$ | H | $C_6H_5$ | |
| 4 | $CH_2OCH_3$ | H | H | $C_6H_5$ | |
| 5 | $CH_2OCH_3$ | $CH_2CH_2OH$ | H | $C_6H_5$ | m.p. 118–120° C. |
| 6 | $C_3H_7$—n | H | H | $C_6H_5$ | |
| 7 | $CH_2OCH_3$ | H | H | $C_4H_9$—n | |
| 8 | $CH_2OCH_3$ | $C_3H_7$—n | H | $C_6H_5$ | |
| 9 | $C_3H_7$—n | $CH_3$ | H | $C_6H_5$ | |
| 10 | $CH_2OCH_3$ | $CH_2CH_2SH$ | H | $C_6H_5$ | |
| 11 | $CH_2OCH_3$ | $CH_3$ | H | $CH_3$ | m.p. 136–137° C. |
| 12 | $C_3H_7$—n | $C_2H_5$ | H | $C_6H_5$ | |
| 13 | $CH_2OCH_3$ | $CH_2CH_2OH$ | H | $C_4H_9$—n | m.p. 62–68° C. |
| 14 | $CH_2OCH_3$ | $CH_2CH_2Cl$ | H | $C_6H_5$ | |
| 15 | $CH_2OCH_3$ | $CH_3$ | H | $C_4H_9$—n | m.p. 60–62° C. |
| 16 | $CH_2OCH_3$ | $CH_3$ | $CH_3$ | $C_4H_9$—n | |
| 17 | $C_3H_7$—n | $C_3H_7$—n | H | $C_6H_5$ | |
| 18 | $CH_2OCH_3$ | $C_2H_5$ | H | $C_4H_9$—n | |
| 19 | $CH_2OCH_3$ | $CH_2CH_2OCH_3$ | H | $C_6H_5$ | |
| 20 | $C_3H_7$—n | $CH_2CH_2OH$ | H | $C_6H_5$ | |
| 21 | $CH_2OCH_3$ | $CH_2CH_2OH$ | H | $CH_3$ | m.p. 147–149° C. |
| 22 | $CH_2Cl$ | $CH_2CH_2OH$ | H | $CH_3$ | |
| 23 | $C_3H_7$—n | $CH_2CH_2OCH_3$ | H | $C_6H_5$ | |
| 24 | $CH_2OCH_3$ | $CH_2CH_2OC_2H_5$ | H | $C_6H_5$ | |
| 25 | $CH_2OCH_3$ | $CH_2CH_2Cl$ | H | $C_4H_9$—n | |
| 26 | $CH_2OCH_3$ | $CH_2CH_2OCH_3$ | H | $CH_3$ | |

TABLE 1-continued

Compounds of the formula $$R_1-\underset{\underset{C_6H_3(CH_3)_2(2,6)}{|}}{\overset{\overset{O}{\|}}{C}}-N-\underset{\underset{R_7}{|}}{\overset{R_3}{|}}\underset{}{C}-\underset{}{\overset{R_4}{|}}\underset{}{C}-\overset{\overset{O}{\|}}{C}-O-\underset{\underset{R_7}{|}}{\overset{R_6}{|}}Sn-R_6$$

wherein $R_5 = R_6 = R_7$

| Comp. | $R_1$ | $R_3$ | $R_4$ | $R_{5,6,7}$ | Physical constants |
|---|---|---|---|---|---|
| 27 | $C_3H_7-n$ | $C_2H_4OC(=O)-NHC_3H_7-i$ | H | $C_6H_5$ | |
| 28 | $CH_2OCH_3$ | $CH_2CH_2OCH_3$ | H | $C_4H_9-n$ | |
| 29 | $CH_2OCH_3$ | H | H | $CH_3$ | |
| 30 | $CH_2OCH_3$ | $CH_2CH_2SCH_3$ | H | $C_6H_5$ | |
| 31 | $CH_2Cl$ | H | H | $C_6H_5$ | |
| 32 | $CH_2OCH_3$ | $CH_2CH_2OCH_2OCH_3$ | H | $C_6H_5$ | |
| 33 | $CH_2Cl$ | $CH_3$ | H | $C_6H_5$ | |
| 34 | $CH_2Cl$ | $CH_2CH_2OH$ | H | $C_6H_5$ | resin |
| 35 | $CH_2Cl$ | $CH_3$ | $CH_3$ | $C_4H_9-n$ | |
| 36 | $CH_2Cl$ | $CH_2CH_2Cl$ | H | $C_6H_5$ | |
| 37 | Benzyl | H | H | $C_6H_5$ | |
| 38 | $CH_2Cl$ | $C_2H_5$ | H | cyclohexyl | |
| 39 | Benzyl | $CH_3$ | H | $C_6H_5$ | |
| 40 | $CH_2Cl$ | H | H | cyclohexyl | |
| 41 | Benzyl | $CH_2CH_2OH$ | H | $C_6H_5$ | |
| 42 | $CH_2OCH_3$ | $CH_2CH_2OC(=O)CH_3$ | H | $C_6H_5$ | |
| 43 | $CH_2Cl$ | $CH_3$ | H | cyclohexyl | |
| 44 | Benzyl | $CH_2CH_2OCH_3$ | H | $C_6H_5$ | |
| 45 | $CH_2CH_2Cl$ | H | H | $C_6H_5$ | |
| 46 | $CH_2OCH_3$ | $C_2H_4OC(=O)NHCH_3$ | H | $C_6H_5$ | |
| 47 | $CH_2OH$ | $CH_3$ | H | $C_6H_5$ | |
| 48 | $CH_2OCH_3$ | $C_2H_4OC(=O)NHC_3H_7-i$ | H | $C_6H_5$ | |
| 49 | $CH_2OCH_3$ | $C_2H_4OC(=O)OC_2H_5$ | H | $C_6H_5$ | |
| 50 | $CH_2OC_2H_5$ | $CH_3$ | $CH_3$ | cyclohexyl | |
| 51 | $CH_2OCH_3$ | $C_2H_5$ | H | cyclohexyl | |
| 52 | $CH_2OCH_3$ | $CH_2CH_2OH$ | H | cyclohexyl | |
| 53 | $CH_2OC_2H_5$ | $CH_2CH_2OH$ | H | $C_6H_5$ | |
| 54 | $CH_2OCH_2CH=CH_2$ | $CH_3$ | $CH_3$ | cyclohexyl | |
| 55 | $CH_2OCH_2CH=CH_2$ | $CH_3$ | H | $C_6H_5$ | |
| 56 | $CH_2OCH_2CH=CH_2$ | $CH_2CH_2OH$ | H | $C_6H_5$ | |
| 57 | $CH_2OCH_2C\equiv CH$ | $CH_3$ | H | $C_6H_5$ | |
| 58 | $CH_2OCH_2C\equiv CH$ | $CH_2CH_2OH$ | H | $C_6H_5$ | |
| 59 | $CH_2OCH_2C\equiv CH$ | $CH_2CH_2OCH_3$ | H | $C_6H_5$ | |
| 60 | $CH_2OC_6H_5$ | $CH_3$ | H | $C_6H_5$ | |
| 61 | $CH_2OC_6H_5$ | $CH_2CH_2OH$ | H | $C_6H_5$ | |
| 62 | $CH_2O$ benzyl | H | H | $CH_3$ | |
| 63 | $CH_2O$ benzyl | $CH_3$ | H | $C_6H_5$ | |
| 64 | $CH_2O$ benzyl | $CH_2CH_2OH$ | H | $C_6H_5$ | |
| 65 | $CH_2OCH_2OC_2H_5$ | $CH_3$ | H | $C_4H_9-n$ | |
| 66 | $CH_2OCH_2OC_2H_5$ | $CH_2CH_2OH$ | H | $C_6H_5$ | |
| 67 | $CH_2OC_2H_4OCH_3$ | $CH_3$ | H | cyclohexyl | |
| 68 | $CH_2OC_2H_4OCH_3$ | $CH_2CH_2OH$ | H | $C_6H_5$ | |
| 69 | $CH_2OSO_2CH_3$ | H | H | $C_6H_5$ | |
| 70 | $CH_2OSO_2CH_3$ | $CH_3$ | H | cyclohexyl | |
| 71 | $CH_2OSO_2CH_3$ | $CH_2CH_2OH$ | H | $C_4H_9-n$ | |
| 72 | $CH_2OSO_2CH_3$ | $CH_2CH_2Cl$ | H | $CH_3$ | |
| 73 | $CH_2OSO_2NHCH_3$ | H | H | $C_6H_5$ | |
| 74 | $CH_2OSO_2NHCH_3$ | $CH_3$ | H | $C_6H_5$ | |
| 75 | $CH_2OSO_2NHCH_3$ | $CH_2CH_2OH$ | H | cyclohexyl | |
| 76 | $CH_2SCH_3$ | $CH_3$ | $CH_3$ | $C_6H_5$ | |
| 77 | $CH_2SCH_3$ | $CH_3$ | H | $C_6H_5$ | |
| 78 | $CH_2SCH_3$ | $CH_2CH_2OH$ | H | $C_4H_9-n$ | |
| 79 | $CH_2SOCH_3$ | $CH_3$ | H | $C_6H_5$ | |
| 80 | $CH_2SO_2CH_3$ | $CH_3$ | H | $C_6H_5$ | |
| 81 | $CH_2SO_2CH_3$ | H | H | $C_6H_5$ | |

TABLE 1-continued

Compounds of the formula $$R_1-\overset{O}{\underset{\|}{C}}-\underset{\underset{C_6H_3(CH_3)_2(2,6)}{|}}{N}-\overset{R_3}{\underset{}{C}}\diagdown\overset{R_4}{\underset{}{\diagup}}\overset{O}{\underset{\|}{C}}-C-O-\underset{\underset{R_7}{|}}{\overset{\overset{R_6}{|}}{Sn}}-R_6$$

wherein $R_5 = R_6 = R_7$

| Comp. | $R_1$ | $R_3$ | $R_4$ | $R_{5,6,7}$ | Physical constants |
|---|---|---|---|---|---|
| 82 | $CH_2SO_2C_2H_5$ | $CH_2CH_2OH$ | H | cyclohexyl | |
| 83 | $CH_2-N\diagup\!\!\!\diagdown$ (imidazolyl) | $CH_3$ | H | $C_6H_5$ | |
| 84 | $CH_2-N\diagup\!\!\!\diagdown$ (imidazolyl) | $CH_2CH_2OH$ | H | $C_6H_5$ | |
| 85 | $CH_2-N\diagup\!\!\!\diagdown$ (triazolyl) | $CH_3$ | H | $C_6H_5$ | |
| 86 | $CH_2-N\diagup\!\!\!\diagdown$ (triazolyl) | $CH_3$ | H | $C_6H_5$ | |
| 87 | $CH_2-CH=CH-CH_3$ | $CH_3$ | H | $C_6H_5$ | |
| 88 | $CH_2-CH=CH-CH_3$ | $CH_2CH_2OH$ | H | $C_6H_5$ | |
| 89 | cyclopropyl | H | H | $C_6H_5$ | |
| 90 | 2-furyl | $CH_3$ | H | $C_6H_5$ | |
| 91 | 2-tetrahydrofuryl | H | H | $C_4H_9-n$ | |
| 92 | cyclopropyl | $CH_3$ | H | $CH_3$ | |
| 93 | 2-furyl | $CH_2CH_2OH$ | H | $C_6H_5$ | |
| 94 | cyclopropyl | $C_2H_5$ | $CH_3$ | $C_6H_5$ | |
| 95 | cyclopropyl | $CH_2CH_2OH$ | H | $C_6H_5$ | |
| 96 | 2-tetrahydrofuryl | $CH_3$ | H | $C_6H_5$ | |
| 97 | 2-tetrahydrofuryl | $CH_2CH_2OH$ | H | $C_6H_5$ | |
| 98 | 2-tetrahydrofuryl | $CH_2CH_2OCH_3$ | $CH_3$ | cyclohexyl | |
| 99 | 2-tetrahydrofuryl | $CH_2CH_2OCCH_3$ | H | $C_6H_5$ | |

Formulation Examples for liquid active ingredients of the formula I (%=percent by weight)

1. Emulsion concentrates

| | (a) | (b) | (c) |
|---|---|---|---|
| active ingredient from Table | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

2. Solutions

| | (a) | (b) | (c) | (d) |
|---|---|---|---|---|
| active ingredient from Table | 80% | 10% | 5% | 95% |
| ethylene glycol-monomethyl ether | 20% | — | — | — |
| polyethylene glycol (MW 400) | — | 70% | — | — |
| N—methyl-2-pyrrolidone | — | 20% | — | — |
| epoxidised coconut oil | — | — | 1% | 5% |
| ligroin (boiling limits 160-190° C.) | — | — | 94% | — |

The solutions are suitable for application in the form of very fine drops.

3. Granulates

| | (a) | (b) |
|---|---|---|
| active ingredient from Table | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

4. Dusts

| | (a) | (b) |
|---|---|---|
| active ingredient from Table | 2% | 5% |
| highly dispersed silicic acid | 1% | 5% |
| talcum | 97% | — |

-continued

| 4. Dusts | (a) | (b) |
|---|---|---|
| kaolin | — | 90% |

Ready-for-use dusts are obtained by the intimate mixing together of the carriers with the active ingredient.

Formulation Examples for solid active ingredients of the formula I (%=percent by weight)

| 5. Wettable powders | (a) | (b) | (c) |
|---|---|---|---|
| active ingredient from Table | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 6. Emulsion concentrate | |
|---|---|
| active ingredient from Table | 10% |
| octylphenol polyethylene glycol ether (4–5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active ingredient from Table | 5% | 8% |
| talcum | 95% | — |
| kaolin | — | 92% |

Dusts ready for use are obtained by mixing the active ingredient with the carriers and grinding the mixture in a suitable mill.

| 8. Extruder granulate | |
|---|---|
| active ingredient from Table | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| 9. Coated granulate | |
|---|---|
| active ingredient from Table | 3% |
| polyethylene glycol (MG 200) (MG = molecular weight) | 3% |
| kaolin | 94% |

The finely ground active ingredient is evenly applied, in a mixer, to the kaolin moistened with polyethylene glycol. Dustfree coated granules are obtained in this manner.

| 10. Suspension concentrate | |
|---|---|
| active ingredient from Table | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

BIOLOGICAL EXAMPLES

EXAMPLE 11

Action against Puccinia graminis on wheat (a) Residual-protective action

Six days after being sown, wheat plants were sprayed with a spray liquor prepared from wettable powder of the active substance (0.06% of active substance). After 24 hours, the treated plants were infested with a uredospore suspension of the fungus. After an incubation time of 48 hours at about 20° C. with 95–100% relative humidity, the infested plants were kept in a greenhouse at about 22° C. An assessment of the development of rust pustules was made 12 days after infestation.

(b) Systemic action

A spray liquor prepared from wettable powder of the active substance (0.006% of active substance, relative to the volume of soil) was poured onto the soil of wheat plants 5 days after sowing. After 48 hours, the treated plants were infested with a uredospore suspension of the fungus. After an incubation time of 48 hours at about 20° C. with 95–100% relative humidity, the infested plants were kept in a greenhouse at about 22° C. An assessment of the development of rust pustules was made 12 days after infestation.

Compounds listed in the Table exhibited against Puccinia fungus a good action. Untreated but infested control plants displayed a level of Puccinia infection of 100%. Among other compounds giving good results, the compounds Nos. 2, 11 and 21 reduced Puccinia infection to 0 to 5%.

EXAMPLE 12

Action against Cercospora arachidicola on groundnut plants (a) Residual-protective action Groundnut plants 10–15 cm in height were sprayed with a spray liquor produced from wettable powder of the active substance (0.006% of active substance); and 48 hours later they were infested with a conidiospore suspension of the fungus. The infested plants were incubated for 72 hours at about 21° C. with high relative humidity, and were subsequently kept in a greenhouse until the typical leaf spots had appeared. The assessment of the fungicidal action was made 12 days after infestation, and was based on the number and size of the occurring spots.

(b) Systemic action

A spray liquor prepared from wettable powder of the active substance (0.06% of active substance, relative to the volume of soil) was poured onto the soil of groundnut plants 10–15 cm in height. After 48 hours, the treated plants were infested with a conidiospore suspension of the fungus, and were subsequently incubated for 72 hours at about 21° C. with high relative humidity. The plants were then kept in a greenhouse, and an assessment of the extent of fungus infection was made after 11 days.

Compared with untreated, but infested control plants (number and size of spots=100%), groundnut plants which had been treated with active substances from the Table exhibited a greatly reduced level of Cercospora infection. Thus, the compounds Nos. 2, 5, 11, 13 and 15 prevented the occurrence of spots in the above tests almost completely (0–10%).

EXAMPLE 13

Action against Erysiphae graminis on barley (a) Residual-protective action

Barley plants about 8 cm in height were sprayed with a spray liquor prepared from wettable powder of the active substance (0.06% of active substance). After 3–4 hours, the treated plants were dusted with conidiospores of the fungus. The infested barley plants were kept in a greenhouse at about 22° C., and the extent of fungus infection was assessed after 10 days.

(b) Systemic action

A spray liquor prepared from wettable powder of the active substance (0.02% of active substance, relative to the volume of soil) was poured onto the soil of barley plants about 8 cm in height. Care was taken to ensure that the spray liquor did not come into contact with the parts of the plants above the soil. After 48 hours, the treated plants were dusted with conidiospores of the fungus. The infested barley plants were kept in a greenhouse at about 22° C., and an assessment of the extent of fungus infection was made after 10 days.

Compounds of the formula I exhibited an action against Erysiphe fungus. Untreated but infested control plants displayed a level of Erysiphe infection of 100%. Among other effective compounds shown in the Table, the compound No. 2 reduced fungus infection on barley to 0 to 5%.

EXAMPLE 14

Residual-protective action against Venturi inaequalis on apple shoots

Apple seedlings having 10–20 cm long fresh shoots were sprayed with a spray liquor prepared from wettable powder of the active substance (0.06% of active substance). The treated plants were sprayed after 24 hours with a conidiospore suspension of the fungus. The plants were then incubated for 5 days with 90–100% relative humidity, and for a further 10 days they were kept at 20°–24° C. in a greenhouse. The extent of scab infection was assessed 15 days after infestation.

Compounds Nos. 2 and 5 reduced infection to less than 10%, whereas untreated but infested control shoots had suffered a 100% level of infection.

EXAMPLE 15

Action against Botrytis cinerea on beans

Residual-protective action

Bean plants about 10 cm in height were sprayed with a spray liquor prepared from wettable powder of the active substance (0.02% of active substance). The plants were infested after 48 hours with a conidiospore suspension of the fungus. The extent of fungus infection was assessed after incubation of the infested plants for 3 days at 21° C. with 95–100% relative humidity. The compounds listed in the Table greatly reduced fungus infection in many cases. At a concentration of 0.02%, the compound No. 2 for example proved fully effective. The level of infection was 0 to 8%.

The Botrytis infection on untreated but infested plants was 100%.

EXAMPLE 16

Action against Phytophthora infestans on tomato plants (a) Residual-protective action Tomato plants were sprayed, after 3-weeks' cultivation, with a spray liquor produced from wettable powder of the active substance (0.06% of active substance). After 24 hours, the treated plants were infested with a suspension of sporangia of the fungus. An assessment of the fungus infection was made after incubation of the infested plants during 5 days at 20° C. with 90°–100° relative humidity.

(b) Systemic action

A spray liquor prepared from wettable powder of the active substance (0.06% of active substance, relative to the volume of soil) was applied to the soil in which tomato plants had been cultivated for 3 weeks. Care was taken to ensure that the spray liquor did not come into contact with the parts of the plants above the soil. After 48 hours, the treated plants were infested with a suspension of sporangia of the fungus. An assessment of fungus infection was made after incubation of the infested plants during 5 days at 20° C. with 90–100% relative humidity.

Among other effective compounds in the above test, the compounds Nos. 2, 5 and 13 exhibited a very good Phytophthora action. Compared with the infection occurring on untreated control plants (100% infection), infection after treatment with these compounds had been prevented practically completely (0 to 5%).

EXAMPLE 17

Grain preservative test (a) Short-duration test against mould fungi on moist maize Dry maize grains intended for animal feed (80 g portions) were thoroughly mixed, in closable plastic beakers, with active substances of the formula I in the form of an aqueous suspension, emulsion or solution. The application of the substance was adjusted to give a concentration of 0.06% of active substance, relative to the dry weight of the maize. A moistened paper strip provided a moisture-saturated atmosphere in each beaker filled with maize and subsequently closed. After an incubation time of 2-3 weeks at about 20° C., there developed spontaneously in the case of the maize specimens treated only with water a mixed population of mould fungi, and no artificial infestation was necessary. The extent of the development of fungi after 3 weeks served as a basis for evaluating the effectiveness of the compounds of the formula I.

(b) Long-duration test against mould fungi on moist maize

I. The maize specimens which exhibited no fungus infestation after 3 weeks were incubated for a further two months. A visual assessment was made after each month using the same criteria as in test (a).

II. The test procedure was basically the same as under (a) and (b), except that the substance to be tested was tested at concentrations of 2000, 600 and 200 ppm of active substance (relative to the dry weight of maize) for 6 months.

As a result of treatment with active substances of the formula I, especially with the compounds Nos. 5, 13, 15, 20 and 21, the formation of mould fungi on moist maize was completely prevented in all three tests a, bI and bII, both in the short term (3 weeks) and in the long term (6 months). Even with a test concentration of 200 ppm of AS, the maize exhibited virtually no infection after 6 months.

In similar tests, in which fodder grain (oats), hay, beet chips and broad beans were used in place of fodder maize, similar results provided evidence of prolonged protection over several months after treatment with the above active substances.

The untreated comparative specimens were all completely mouldy and uneatable.

What is claimed is:

1. A compound of the formula

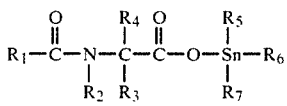

wherein $R_1$ is lower alkyl or lower alkyl substituted by a substituent selected from the group consisting of hydroxy, $C_1$-$C_6$-alkoxy, $C_3$-$C_4$-alkenyloxy, $C_1$-$C_3$-alkoxy-($C_1$-$C_3$-alkoxy), $C_1$-$C_6$-alkylthio, $C_1$-$C_4$-alkylsulfonyloxy, $C_1$-$C_4$-alkylaminosulfonyloxy, $C_1$-$C_4$-alkylsulfonyl, $C_1$-$C_4$-alkylsulfoxy, halogen, phenyl, phenoxy, benzyloxy and azolyl; lower alkenyl halogen-substituted alkenyl; cycloalkyl or halogen-substituted cycloalkyl;

$R_2$ is aryl or aryl substituted by a substituent selected from the group consisting of halogen, $C_1$-$C_3$-alkoxy, $C_1$-$C_3$-alkyl and $C_1$-$C_3$-haloalkyl;

$R_3$ and $R_4$ independently of one another are each hydrogen; or lower alkyl or lower alkyl substituted by a substituent selected from the group consisting of hydroxy, $C_1$-$C_6$-alkoxy, $C_3$-$C_4$-alkenyloxy, $C_1$-$C_3$-alkoxy-($C_1$-$C_3$-alkoxy), $C_1$-$C_6$-alkylthio, $C_1$-$C_4$-alkylsulfonyloxy, $C_1$-$C_4$-alkylaminosulfonyloxy, $C_1$-$C_4$-alkylsulfonyl, $C_1$-$C_4$-alkylsulfoxy, halogen, phenyl, phenoxy, benzyloxy and azolyl; and $R_5$, $R_6$ and $R_7$ independently of one another are each lower alkyl or lower alkyl substituted by a substituent selected from the group consisting of hydroxy, $C_1$-$C_6$-alkoxy, $C_3$-$C_4$-alkenyloxy, $C_1$-$C_3$-alkoxy-($C_1$-$C_3$-alkoxy), $C_1$-$C_6$-alkylthio, $C_1$-$C_4$-alkylsulfonyloxy, $C_1$-$C_4$-alkylaminosulfonyloxy, $C_1$-$C_4$-alkylsulfonyl, $C_1$-$C_4$-alkylsulfoxy, halogen, phenyl, phenoxy, benzyloxy and azolyl; cycloalkyl or halogen-substituted cycloalkyl; or aryl or aryl substituted by a substituent selected from the group consisting of halogen, $C_1$-$C_3$-alkoxy, $C_1$-$C_3$-alkyl and $C_1$-$C_3$-haloalkyl.

2. A compound according to claim 1, wherein $R_1$ is methyl substituted by chlorine, methoxy, ethoxy, $CH_2$=$CHCH_2O$—, $HC$≡$CCH_2O$—, $CH_3OCH_2O$—, methylsulfonyl, methylsulfonyloxy, methylaminosulfonyloxy or methylthio or $R_1$ is $C_2$-$C_4$-alkenyl, $C_2$-$C_4$-alkenyl substituted by chlorine, or it is $C_3$-$C_6$-cycloalkyl, $R_2$ is phenyl which is substituted in both ortho-positions, and optionally additionally in the meta position, by chlorine, methyl, methoxy, —$CF_3$ and/or nitro, or $R_2$ is α-naphthyl substituted in the ortho-position by chlorine, methyl, methoxy, —$CF_3$ or nitro, $R_3$ is hydrogen, $C_1$-$C_2$-alkyl, hydroxyethyl, methoxyethyl, methoxymethyl or chloroethyl, $R_4$ is hydrogen, and $R_5$, $R_6$ and $R_7$ independently of one another are each methyl, n-butyl, cyclohexyl or phenyl.

3. A compound according to claim 2, wherein $R_1$ is methyl substituted by chlorine, methoxy, ethoxy, $CH_2$=$CHCH_2O$—, $HC$≡$CCH_2O$— or methoxymethoxy or $R_1$ is cyclopropyl, and $R_2$ is phenyl diortho-substituted by chlorine, methyl, methoxy, $CF_3$ and/or nitro.

4. A compound according to claim 1, wherein $R_1$ is methoxymethyl, $R_2$ is phenyl diortho-substituted by chlorine, methyl, methoxy, $CF_3$ and/or nitro, $R_3$ is methyl or hydroxymethyl, $R_4$ is hydrogen, and $R_5$, $R_6$ and $R_7$ independently of one another are each $C_1$-$C_4$-alkyl, $C_3$-$C_6$-cycloalkyl or phenyl.

5. A compound according to claim 4, wherein $R_2$ is 2,6-dimethylphenyl, and $R_5$, $R_6$ and $R_7$ are each $C_1$-$C_4$-alkyl or phenyl.

6. A compound selected from the group consisting of:

N-(1'-triphenyltinoxycarbonylethyl)-N-methoxyacetyl-2,6-dimethylaniline,

N-[1'-triphenyltinoxycarbonyl-(prop-3-ol-1-yl)]-N-methoxyacetyl-2,6-dimethylaniline, N-(1'-trimethyltinoxycarbonylethyl)-N-methoxyacetyl-2,6-dimethylaniline, N-[1'-tri-n-butyltinoxycarbonyl-(prop-3-ol-1-yl)]-N-methoxyacetyl-2,6-dimethylaniline, N-(1'-tri-n-butyltinoxycarbonylethyl)-N-methoxyacetyl-2,6-dimethylaniline, and N-[1'-trimethyltinoxycarbonyl-(prop-3-ol-1-yl)]-N-methoxyacetyl-2,6-dimethylaniline.

7. A pesticidal composition for controlling and/or preventing an infestation of plants by phytopathogenic fungi, bacteria or insects, which composition comprises, as at least one active ingredient, a compound according to claim 1 and a carrier.

8. A method for controlling or preventing an infestation of cultivated plants by phytopathogenic pests, which comprises applying a pesticidally effective amount of a compound as claimed in claim 1 to the plant to be protected or to the locus thereof.

9. A process for controlling or preventing an infestation of cultivated plants by phytopathogenic pests, which comprises applying a pesticidally effective amount of a compound as claimed in claim 2 to the plant to be protected or to the locus thereof.

10. A process for controlling or preventing an infestation of cultivated plants by phytopathogenic pests, which comprises applying a pesticidally effective amount of a compound as claimed in claim 3 to the plant to be protected or to the locus thereof.

11. A process for controlling or preventing an infestation of cultivated plants by phytopathogenic pests, which comprises applying a pesticidally effective amount of a compound as claimed in claim 4 to the plant to be protected or to the locus thereof.

12. A process for controlling or preventing an infestation of cultivated plants by phytopathogenic pests, which comprises applying a pesticidally effective amount of a compound as claimed in claim 5 to the plant to be protected or to the locus thereof.

13. A process for controlling or preventing an infestation of cultivated plants by phytopathogenic pests, which comprises applying a pesticidally effective amount of a compound as claimed in claim 6 to the plant to be protected or to the locus thereof.

14. The compound according to claim 6 which is N-(1'-triphenyltinoxycarbonylethyl)-N-methoxyacetyl-2,6-dimethylaniline.

15. The compound according to claim 6 which is N-[1'-triphenyltinoxycarbonyl-(prop-3-ol-1-yl)]-N-methoxyacetyl-2,6-dimethylaniline.

* * * * *